(12) United States Patent  
Tronnes (10) Patent No.: US 8,489,189 B2  
(45) Date of Patent: Jul. 16, 2013

(54) EXPANDABLE FIXATION MECHANISM

(75) Inventor: Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 2464 days.

(21) Appl. No.: 10/977,500

(22) Filed: Oct. 29, 2004

(65) Prior Publication Data

US 2006/0095078 A1    May 4, 2006

(51) Int. Cl.
*A61N 1/18*    (2006.01)

(52) U.S. Cl.
USPC ............................................................ 607/36

(58) Field of Classification Search
USPC .............................. 607/36, 119, 126, 127, 128
See application file for complete search history.

(56) References Cited

U.S. PATENT DOCUMENTS

| | | | | |
|---|---|---|---|---|
| 3,811,423 | A | | 5/1974 | Dickinson |
| 3,902,501 | A | * | 9/1975 | Citron et al. ............... 607/126 |
| 4,269,198 | A | | 5/1981 | Stokes |
| 4,658,835 | A | | 4/1987 | Pohndorf |
| 4,768,523 | A | | 9/1988 | Cahalan et al. |
| 4,943,618 | A | | 7/1990 | Stoy et al. |
| 5,190,052 | A | * | 3/1993 | Schroeppel ................ 607/123 |
| 5,252,692 | A | | 10/1993 | Lovy et al. |
| 5,300,107 | A | | 4/1994 | Stokes et al. |
| 5,405,367 | A | | 4/1995 | Schulman et al. |
| 5,545,206 | A | | 8/1996 | Carson |
| 5,662,698 | A | * | 9/1997 | Altman et al. ............. 607/123 |
| 5,800,499 | A | * | 9/1998 | Ollivier ..................... 607/126 |
| 5,837,007 | A | | 11/1998 | Altman et al. |
| 5,908,447 | A | | 6/1999 | Schroeppel et al. |
| 5,951,597 | A | | 9/1999 | Westlund et al. |
| 5,957,966 | A | | 9/1999 | Schroeppel et al. |
| 6,164,284 | A | * | 12/2000 | Schulman et al. ............. 128/899 |
| 6,168,624 | B1 | | 1/2001 | Sudai |
| 6,181,973 | B1 | | 1/2001 | Ceron et al. |
| 6,240,321 | B1 | | 5/2001 | Janke et al. |
| 6,240,322 | B1 | | 5/2001 | Peterfeso et al. |
| 6,434,431 | B1 | | 8/2002 | Camps et al. |
| 6,542,776 | B1 | | 4/2003 | Gordon et al. |
| 6,650,921 | B2 | | 11/2003 | Spehr et al. |

(Continued)

FOREIGN PATENT DOCUMENTS

DE    3415410 A1 * 10/1984

OTHER PUBLICATIONS

U.S. Appl. No. 10/977,330, entitled "Expandable Fixation Structures," filed Oct. 29, 2004.
Responsive Amendment dated Oct. 11, 2007 for U.S. Appl. No. 10/977,330 (25 pgs.).
Office Action dated Jan. 17, 2008 for U.S. Appl. No. 10/977,330, (14 pgs.).

(Continued)

*Primary Examiner* — Scott Getzow
*Assistant Examiner* — Amanda Patton
(74) *Attorney, Agent, or Firm* — Shumaker & Sieffert, P.A.

(57) ABSTRACT

In general, the invention is directed to a medical device implantable in a body of a patient. The device includes a housing with a plurality of collapsible fixation structures coupled to the housing, and can be in a collapsed configuration or an expanded configuration. The device assumes a collapsed configuration when in the bore of an insertion device, and assumes the expanded configuration when expelled from the insertion device into the body of the patient. The extended fixation structures engage the tissues in the body and restrict migration. One exemplary application of the invention is in the context of a microstimulator, with a pulse generator housed in the housing and one or more electrodes coupled to the housing. The fixation structures help keep the electrodes proximate to the tissues that are to receive the stimulation.

20 Claims, 4 Drawing Sheets

U.S. PATENT DOCUMENTS

| | | | |
|---|---|---|---|
| 6,697,676 B2 | 2/2004 | Dahl et al. | |
| 6,704,605 B2 | 3/2004 | Soltis et al. | |
| 6,714,822 B2 * | 3/2004 | King et al. | 607/117 |
| 7,177,702 B2 | 2/2007 | Wallace et al. | |
| 2002/0072787 A1 | 6/2002 | Partridge et al. | |
| 2002/0077556 A1 | 6/2002 | Schwartz | |
| 2002/0156383 A1 | 10/2002 | Altman et al. | |
| 2002/0156513 A1 | 10/2002 | Borkan | |
| 2003/0229303 A1 | 12/2003 | Haffner | |
| 2003/0236558 A1 * | 12/2003 | Whitehurst et al. | 607/45 |
| 2004/0034401 A1 | 2/2004 | Dahlberg et al. | |
| 2004/0230281 A1 * | 11/2004 | Heil et al. | 607/126 |
| 2004/0230282 A1 | 11/2004 | Cates et al. | |
| 2006/0036307 A1 | 2/2006 | Zarembo et al. | |
| 2006/0095077 A1 | 5/2006 | Tronnes | |

OTHER PUBLICATIONS

Responsive Amendment dated Mar. 17, 2008 for U.S. Appl. No. 10/977,330 (20 pgs.).

Responsive Amendment dated Apr. 17, 2008 for U.S. Appl. No. 10/977,330 (20 pgs.).

Office Action dated May 23, 2008 for U.S. Appl. No. 10/977,330, (12 pgs.).

Responsive Amendment dated Aug. 25, 2008 for U.S. Appl. No. 10/977,330, (18 pgs.).

Office Action dated Dec. 23, 2008 for U.S. Appl. No. 10/977,330, (9 pgs.).

Pre-Appeal Brief Request for Review filed Mar. 23, 2009 for U.S. Appl. No. 10/977,330, 5 pgs.

* cited by examiner

FIG. 7

EXPANDABLE FIXATION MECHANISM

FIELD OF THE INVENTION

The invention relates to medical devices implantable in and near a human or animal body and, more particularly, mechansims for fixation of medical devices.

BACKGROUND

Many implantable medical devices include components that are deployed in particular areas within a human or animal body. In one example, a neurostimulator deployed proximate to targeted tissue includes electrodes that deliver an electrical stimulation therapy to the tissue. In another example, an electrical sensor deployed proximate to a muscle senses activation of the muscle. With these and other implantable devices, it can be desirable that one or more components remain substantially anchored, so that the components will be less likely to migrate from the desired site of sensing or therapy.

Devices that restrict migration of an implanted medical device or a component thereof are called "fixation structures." Fixation structures can anchor a medical device to an anatomical feature, such as an organ or a bone. Fixation structures do not necessarily restrict all motion of the implanted device or its component, but generally reduce the motion of the device or component so that it remains proximate to a target site.

There have been many approaches that address fixation of medical devices. Some devices, such as a lead described in U.S. Pat. No. 4,269,198 to Stokes, employ fixed protrusions such as tines to engage body tissue. Other devices, such as the electrode assembly disclosed in U.S. Pat. No. 6,704,605 to Soltis et al., use a helical securing structure. U.S. Pat. No. 5,405,367 to Schulman et al. describes the use of barbs to hold a medical device such as a microstimulator in place.

Table 1 below lists documents that disclose some of the many devices and techniques pertaining fixation of medical devices. Some of the devices and techniques employ mechanical fixation structures such as tines or swellable membranes. Others employ adhesive properties to hold devices in place.

TABLE 1

| Patent Number | Inventors | Title |
|---|---|---|
| 6,714,822 | King et al. | Apparatus and method for expanding a stimulation lead body in situ |
| 6,704,605 | Soltis et al. | Medical electrode assembly |
| 6,697,676 | Dahl et al. | Medical electrical lead having an expandable electrode assembly |
| 6,650,921 | Spehr et al. | Cardiac lead with minimized inside diameter of sleeve |
| 6,434,431 | Camps et al. | Intramuscular medical electrical lead with fixation member |
| 6,240,322 | Peterfeso et al. | System and apparatus having low profile collapsible tines |
| 6,181,973 | Ceron et al. | Anchoring structures for implantable electrodes |
| 5,951,597 | Westlund et al. | Coronary sinus lead having expandable matrix anchor |
| 5,837,007 | Altman et al. | Intracardiac lead having a compliant fixation device |
| 5,545,206 | Carson | Low profile lead with automatic tine activation |
| 5,405,367 | Schulman et al. | Structure and method of manufacture of an implantable microstimulator |
| 5,300,107 | Stokes et al. | Universal tined myocardial pacing lead |
| 4,658,835 | Pohndorf | Neural stimulating lead with fixation canopy formation |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

In general, the invention is directed to fixation mechanisms for securing medical devices implanted within a human or animal body, as well as medical devices incorporating such fixation mechanisms. Such devices can include implantable neurostimulators, implantable physiological sensors, electrodes, and the like. When the medical devices are implanted, it is generally desirable that migration of an implanted device be restricted. The invention presents implantable devices equipped with fixation mechanisms that help reduce migration.

Various embodiments of the present invention provide solutions to one or more problems existing in the prior art with respect to fixation mechanisms for implantable medical devices. These problems include the migration of medical devices from a desired implantation site. An additional problem is the reduced therapeutic efficacy that may result when a medical device migrates from its intended implantation site. Additional problems relate to the time and skill required in placement of conventional fixation mechanisms, such as sutures, and to the size of conventional fixation mechanisms, which can have a bearing upon techniques for surgical implantation.

Various embodiments of the present invention are capable of solving at least one of the foregoing problems. The invention presents a device that includes a housing with a plurality of collapsible fixation structures coupled to the housing. The device can be in a collapsed configuration or an expanded configuration. When not acted upon by a force, the device assumes the expanded configuration, with the fixation structures extending away from the housing. When inserted into the bore of an insertion device, such as a needle, the fixation structures move close to the housing, and the device assumes the collapsed configuration. When the device is expelled from the insertion device, the fixation structures by their resiliency move toward their expanded positions.

When an insertion device is used to implant the invention in the body of a patient, the extended fixation structures engage the tissues in the body. As a result, migration of the implanted device is restricted. In addition, implantation in some areas of the body causes the body to generate fibrous tissue that adheres to the housing and the fixation structures, thereby further anchoring the device in place.

The invention can be applied as a microstimulator, with a pulse generator housed in the housing and one or more electrodes coupled to the housing. The fixation structures help keep the electrodes proximate to the target tissues, i.e., proximate to the tissues that are to receive the stimulation. As another example, the invention can be applied to physiological sensors.

In comparison to known fixation mechanisms, various embodiments of the invention may provide one or more advantages. For example, the invention can provide reliable fixation for a variety of medical devices, including but not limited to self-contained stimulators, without the need for sutures or other mechanisms requiring surgical placement. Rather, the fixation mechanism is generally self-deploying.

The invention can also be adapted to work with other medical devices, such as lead-mounted electrodes. In addition, the invention provides for a small profile during implantation, allowing implantation to be made by less invasive techniques.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
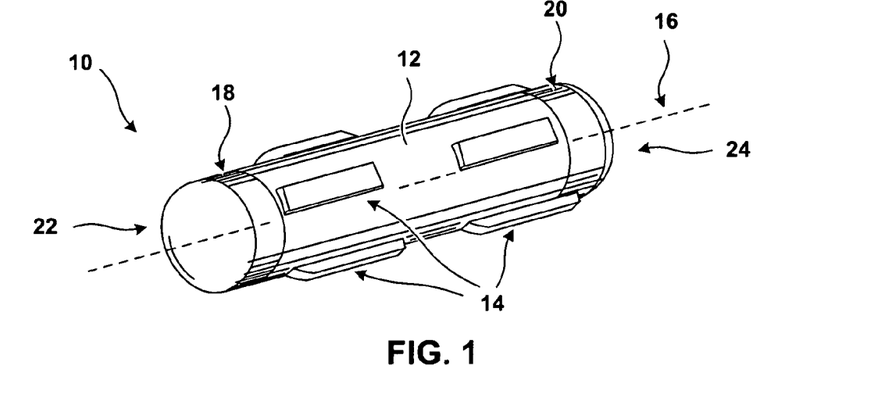
FIG. 1 is a perspective view of an exemplary medical device having collapsible fixation mechanisms in a collapsed state, according to an embodiment of the invention.

FIG. 1 depicts an exemplary medical device 10 configured to be implanted in a human or animal body. For purposes of illustration, FIG. 1 depicts a self-contained device such as a microstimulator or a sensor. The microstimulator may be a neurostimulator or muscle stimulator. The sensor may be configured to sense a variety of conditions, such as pressure, flow, temperature, fluid level, contractile force, pH, chemical concentration, or the like. Medical device 10 is self-contained in that it is not physically coupled to any other medical device by a lead or other connection. Medical device 10 can, for example, receive power from or wirelessly communicate with an external control device. In another embodiment, medical device 10 operates with an internal power supply, such as a rechargeable or non-rechargeable battery. The invention is not limited to any particular medical device. Nor is the invention limited to self-contained medical devices, but encompasses medical devices that include leads or that are otherwise not self-contained.

Exemplary medical device 10 is shown in FIG. 1 in a first, collapsed configuration. Exemplary medical device 10 includes a substantially cylindrical housing 12 and a plurality of collapsible fixation structures 14 coupled to housing 12. In the example of medical device 10, there are eight fixation structures 14 and fixation structures 14 are tines. The invention encompasses devices that include more than eight tines. For example, housing 12 could accommodate an additional four tines in the center of housing 12, offset from the eight tines that are shown.

In FIG. 1, fixation structures 14 are folded against housing 12. In this collapsed configuration, the dimensions of device 10 can be selected such that device 10 can fit inside the bore of an insertion device, such as needle, hollow trocar, endoscope, catheter or cannula. In particular, device 10 can fit through a bore or sleeve oriented substantially parallel to long axis 16. Dimensions of housing 12 can be approximately one to seven millimeters in diameter (transverse to axis 16) and ten to twenty millimeters in length (parallel to axis 16). The invention encompasses other shapes and dimensions as well. The dimensions of medical device 10 can depend upon the internal components of medical device 10. In FIG. 1, for example, medical device 10 can embody a stimulating device, such as a neurostimulator, that delivers electrical stimulations to target tissue via electrodes 18 and 20. Housing 12 is sized to receive the components of a stimulator, such as a pulse generator, wireless telemetry interface, and a power supply.

Figure 2:
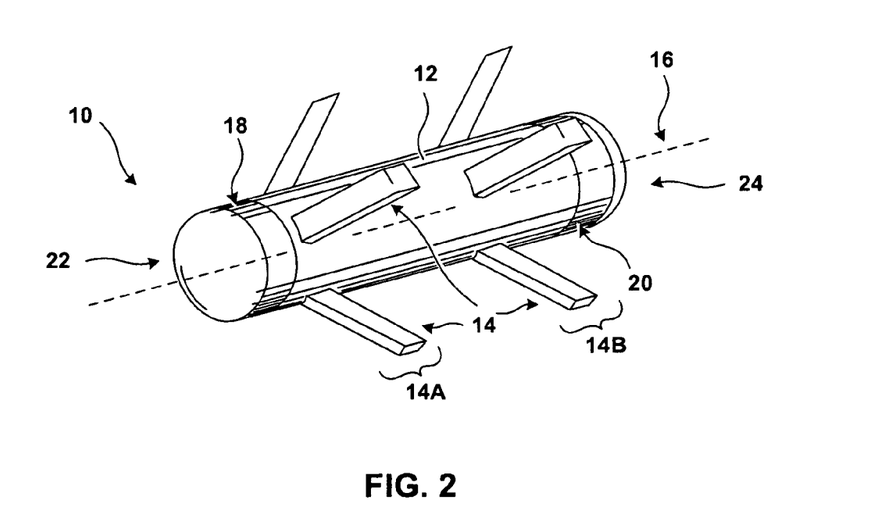
FIG. 2 is a perspective view of the device of FIG. 1 with the fixation mechanisms in an expanded state.

FIG. 2 shows exemplary medical device 10 in a second, expanded configuration. The expanded configuration is the configuration that medical device 10 assumes unless acted upon by a force, such as the reactive force asserted by the bore of an insertion device. As a result, when medical device 10 is expelled in its collapsed state from the insertion device, fixation structures 14 by their resiliency move toward the expanded configuration. It is possible that contact with tissues in the patient's body can prevent fixation structures 14 from becoming fully expanded as depicted in FIG. 2, but it is not necessary that the fixation structures 14 be fully expanded to be effective. As used herein, the "expanded configuration" includes configurations in which fixation structures 14 are wholly or partially expanded.

In the expanded configuration, medical device 10 fixation structures 14 have extended away from axis 16. In particular, fixation structures 14 each extend from housing 12 at an acute angle with respect to axis 16 of medical device 10. In addition, fixation structures 14 extend radially outward from housing 12 in different radial directions. Furthermore, in the embodiment shown in FIG. 2, fixation structures 14 includes first set 14A and second set 14B, which are axially displaced from each other. When extended, fixation structures 14 are more likely to engage surrounding tissue, thereby restricting migration of medical device 10. In addition, deployment of medical device 10 in some sites in the body of the patient causes the body to generate fibrous tissue that adheres to housing 12 and fixation structures 14, thereby further anchoring device 10 in place. In the context of a stimulation device, extension of fixation structures 14 helps hold electrodes 18 and 20 proximate to the target tissues.

Housing 12 can be constructed of any biocompatible material, such as silicone, polyurethane, titanium, stainless steel, fluoropolymer and hydrogel. Housing 12 can also be constructed of another material, and sealed inside an envelope of biocompatible material. Fixation structures 14 likewise can be constructed of one or more biocompatible materials such as silicone, polyurethane, titanium, stainless steel, fluoropolymer and hydrogel. In one embodiment of the invention, fixation structures 14 are formed from a flexible material such as a flexible polymer or metal, and are coupled to housing 12 in the fully expanded position. When inserted into the bore of an insertion device, fixation structures 14 fold down toward housing 12, as shown in FIG. 1. When ejected from the insertion device, fixation structures 14 by their resiliency move toward their fully expanded positions. When fully extended, fixation structures 14 may project one to seven millimeters from housing 12. In actual use, structures such as body tissues proximate to device 10 may prevent fixation structures 14 from achieving the fully expanded configuration.

Fixation structures 14 can be coupled to housing 12 in any manner, such as by adhesive, welding, bonding or interlocking. In some embodiments of the invention, fixation structures 14 can be formed integrally with housing 12.

In a variation, fixation structures 14 can be constructed from a biocompatible hydrogel material. Hydrogel materials that are believed to have wide applicability are the polyacrylonitrile copolymers as described in U.S. Pat. Nos. 4,943,618 and 5,252,692, which are incorporated herein by reference. By controlling relative amounts of copolymers, it is often possible to regulate physical qualities of the hydrogel such as flexibility and amount of expansion. In general, hydrogels can assume a dehydrated state and a hydrated state. A hydrogel element in its dehydrated state is generally substantially smaller than the element in its hydrated state. A hydrogel element in its dehydrated state, when implanted in the body of a patient and placed in contact with body fluids, absorbs water and expands, assuming a hydrated state. Fixation structures 14 made of hydrogel can be coupled to housing 12, and can expand outward and can expand in size when they come in contact with bodily fluids.

Medical device 10 is directionally oriented, with a distal end 22 and a proximal end 24. The portions of tines 14 closest to distal end 22 are affixed to housing 12, and the portions of tines 14 closest to proximal end 24 extend away from housing 12. When medical device 10 is inserted, distal end 22 first, into the bore of an insertion device, tines 14 fold down and medical device 10 assumes a collapsed configuration.

Figure 3:
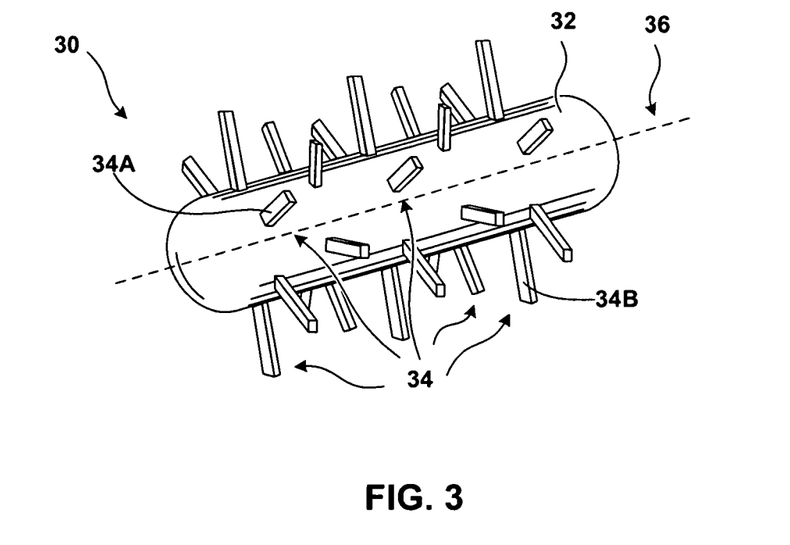
FIG. 3 is a perspective view of another exemplary medical device having collapsible fixation mechanisms in an expanded state, according to an embodiment of the invention.

FIG. 3 is a perspective view of an exemplary medical device 30 in which the fixation structures are not directionally oriented. Like medical device 10, medical device 30 includes a housing 32. Medical device 30 also includes a plurality of fixation structures 34. Fixation structures 34 are tines or spurs that extend outward substantially orthogonally from device axis 34. FIG. 3 shows device 30 in a fully expanded configuration. In the expanded configuration, fixation structures 34 radially extend from housing 32 of device 30. At least some of fixation structures 34 extend in different radial directions. For example, fixation structure 34A extends in a different radial direction than fixation structure 34B. In addition, fixation structures 34A and 34B are axially displaced from each other.

Although medical device 30 has thirty-six tines, the invention encompasses devices having more or fewer tines. Smaller tines can be more flexible than larger tines, and there can be advantages to using a larger number of small tines instead a smaller number of large tines. In addition, medical device has tines arranged in a regular pattern, but the invention supports fixation structures arrayed in an irregular fashion as well.

Housing 32 can be constructed of the same materials as, and have dimensions comparable to, housing 12. Fixation structures 34 can be constructed of the same materials as, and extend as far from the housing as, fixation structures 12. Fixation structures 34, however, are shown as having a thinner profile than fixation structures 12, so that fixation structures 32 can bend toward one end of device 30 or the other.

Medical device 30 need not have distinct proximal and distal ends. When medical device 30 is inserted into the bore of an insertion device, tines 34 fold down, and medical device 10 assumes a collapsed configuration. Device 30 would also assume a collapsed configuration if device 30 were turned end for end and inserted into the bore of the insertion device.

Figure 4:
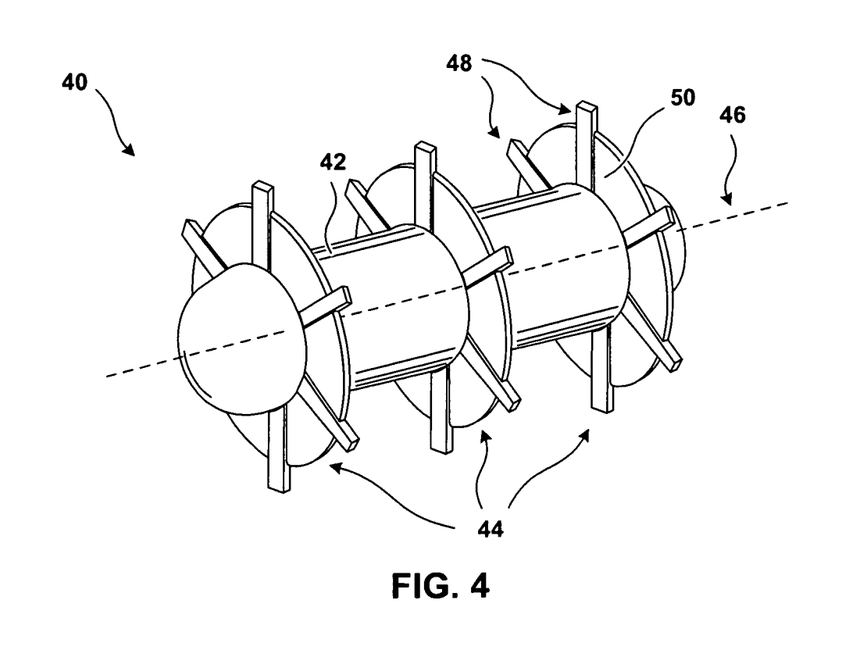
FIG. 4 is a perspective view of a further exemplary medical device having collapsible fixation mechanisms in an expanded state, according to an embodiment of the invention

FIG. 4 is a perspective view of another exemplary embodiment of the invention. Medical device 40 includes a housing 42 and a plurality of fixation structures 44. Fixation structures 44 are flanges that extend outward substantially orthogonally from device axis 44. FIG. 4 depicts three flanges, but the invention encompasses devices having more or fewer flanges as well. FIG. 4 shows device 40 in an expanded configuration.

Like device 30, device 40 includes fixation structures 44 that are not directionally oriented. Either end of medical device 40 could be inserted into the bore of an insertion device, and flanges 44 fold down.

As depicted in FIG. 4, flanges 44 comprise a plurality of ribs 48 with webbing 50 deployed between ribs 48. Webbing 50 may be thinner and more pliable than ribs 48, which can aid in folding of flanges 44. Ribs 48 also protrude farther from axis 46 than webbing 50, which can enhance engagement with fibrous tissue and thereby promote fixation. Ribs 48 and webbing 50 may be, but need not be, constructed from the same material. Although device 40 has eighteen ribs 48, the invention supports embodiments in which there are more or fewer ribs. In some circumstances, there can be advantages to using a larger number of small ribs instead a smaller number of large ribs.

The invention supports embodiments in which flanges do not have ribs and webbing, but have a uniform thickness. The invention also supports embodiments in which fixation structures comprise one or more different types of fixations structures. A medical device may include, for example, both tines and flanges. The fixation structures need not be uniform in size. For example, some tines can be longer than others.

Figure 5:
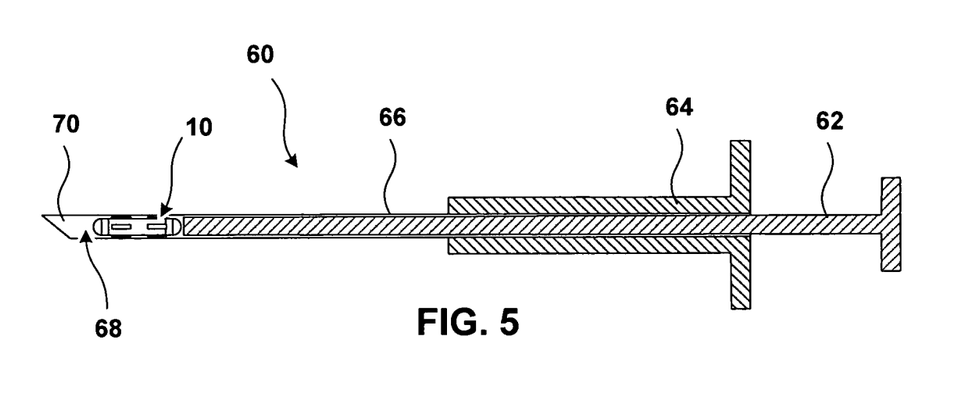
FIG. 5 is a cross section of an exemplary syringe that may be used to implant a device such as the device depicted in FIG. 1.

FIG. 5 is a cross-sectional diagram of an illustrative insertion device 60 that can implant a medical device such as medical device 10 in a patient. Device 60 comprises a syringe, which includes a plunger member 62, a body member 64 and a hollow needle 66 having a bore or lumen 68. Needle 66 is fixedly coupled to body member 64, while plunger member 62 is free to move in lumen 68. Lumen 68 of needle 66 has been enlarged to show medical device 10, in a collapsed configuration, disposed in lumen 68. As depicted in FIG. 5, medical device 10 in the collapsed configuration is an elongated device, shaped substantially like a grain of rice, and sized to fit inside lumen 68. Before placement of medical device 10 into lumen 68, medical device 10 is in an expanded configuration. Placement of medical device 10 into lumen 68 causes medical device 10 to assume the collapsed configuration.

Distal end 70 of needle 66 includes a sharp point that can pierce tissue such as the skin, the mucosa of the gastrointestinal tract, a body organ or a tissue mass. Distal end 70 further includes an opening through which medical device 10 may be expelled from lumen 68 by depressing plunger member 62 with respect to body member 64.

Device 60 is not the only insertion device that can be used to implant a medical device such as medical device 10. For example, a physician can implant medical device 10 by making an incision in the skin, introducing an insertion device such as a catheter into the body of the patient, guiding the insertion device to a target site, pushing medical device 10 through the insertion device, and withdrawing the insertion device.

In general, implantation of a medical device in a collapsed configuration is less invasive than a surgical procedure to implant the medical device in its expanded configuration. The medical device can be delivered to a target site in a collapsed configuration, and expand on its own to its expanded configuration.

Figure 6:
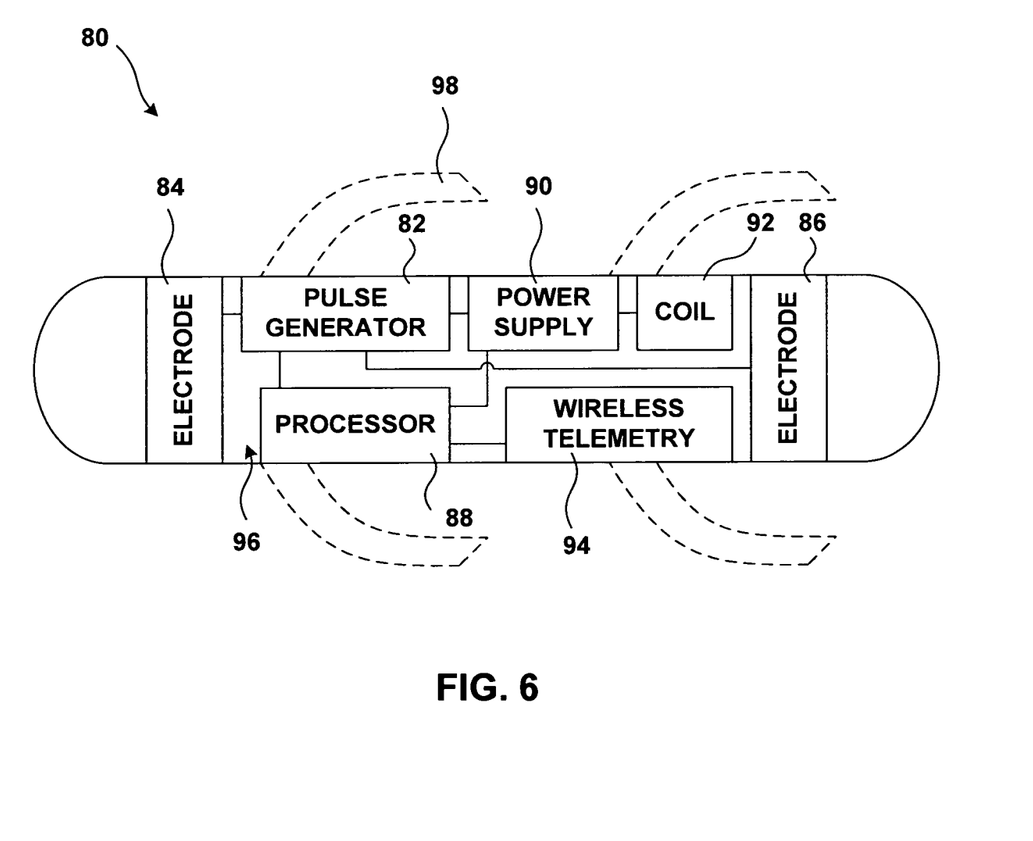
FIG. 6 is a block diagram of an implantable stimulator according to an embodiment of the invention.

FIG. 6 is a block diagram of an exemplary medical device 80 that can employ many of the features described above. Medical device 80 is an example of a self-contained implantable stimulator. Stimulator 80 includes pulse generator 82, which supplies electrical stimulations to the target tissue via electrodes 84, 86, which are exposed to the tissue. Pulse generator 82 supplies stimulations under the direction of processor 88. Processor 88 may comprise a microprocessor, application specific integrated circuit, a programmable logic chip, or other controlling circuitry.

A power supply 90, such as a capacitor or a battery, supplies power to pulse generator 82 and processor 88. In the embodiment depicted in FIG. 6, medical device 80 includes an inductive coil 92 configured to receive energy from an external energy source. Medical device 80 also includes a wireless telemetry interface 94 configured to wirelessly transmit or receive data or instructions. Pulse generator 82, processor 88, power supply 90, coil 92 and wireless telemetry interface 94 are housed inside housing 96.

Fixation structures 98 extend toward an extended position when medical device 80 is implanted in the body of a patient. Extension of fixation structures 98 restricts migration of medical device 80. As a result, electrodes 84, 86 tend to remain proximate to the target tissue.

Medical device 80 can include components other than or in addition to the components depicted in FIG. 6. For example, medical device 80 can incorporate an accelerometer or a sensor, such as a sensor configured to sense conditions such as pressure, flow, temperature, fluid level, contractile force, pH or chemical concentration. The invention is not limited to the specific embodiment depicted in FIG. 6.

In addition, FIG. 6 depicts electronic components such as electrodes as housed inside housing 96. The invention also supports embodiments in which one or more components are deployed on or in fixation structures 98. For example, an electrode can be deployed on the surface of a fixation structure such that the electrode moves away from housing 96 when the fixation structure moves to an expanded configuration.

Figure 7:
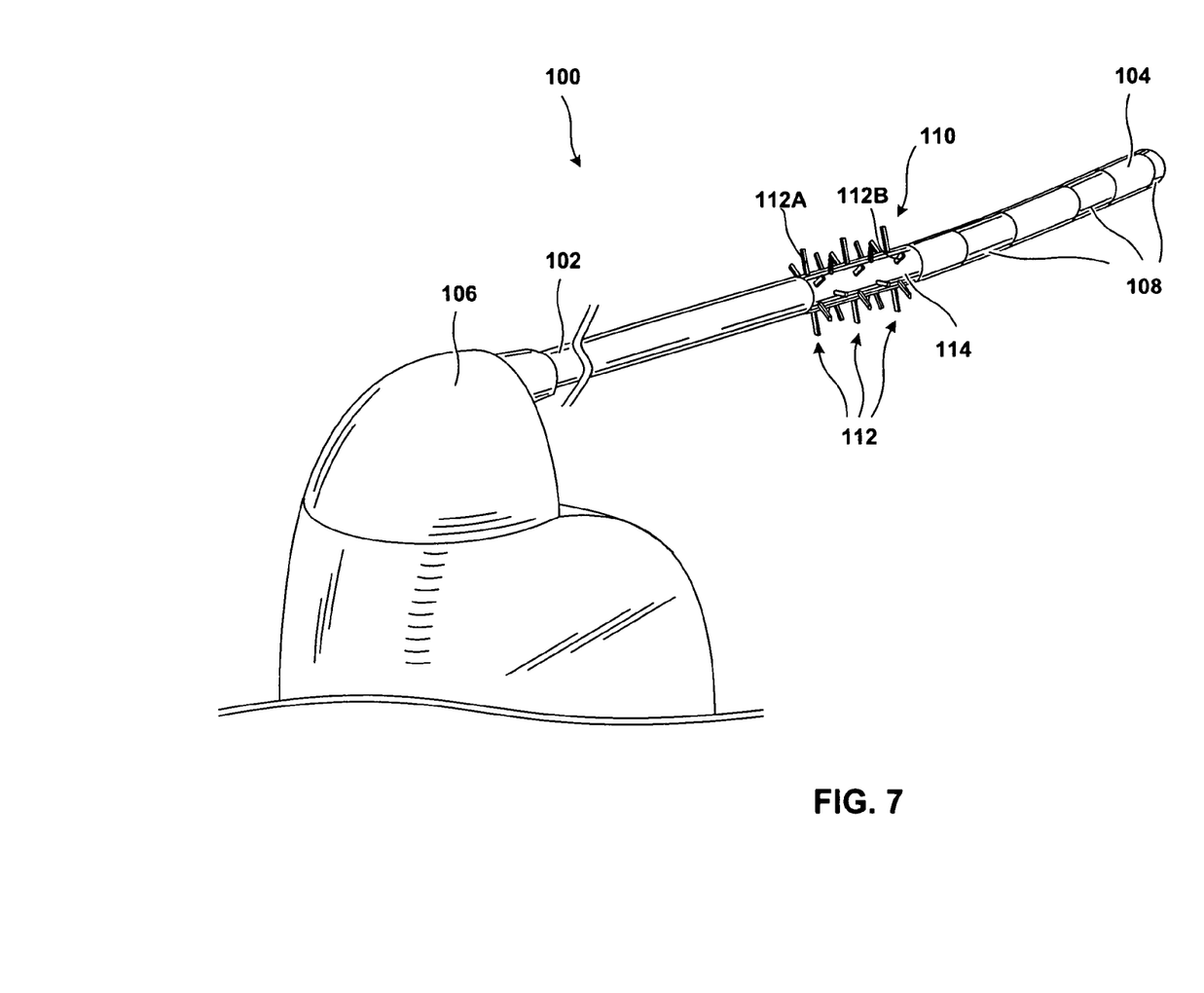
FIG. 7 is a perspective view of a medical device with a device that includes a collapsible fixation mechanism according to another embodiment of the invention.

FIG. 7 is a perspective drawing of a further embodiment of the invention. Extending element 100 is an elongated element having a proximal end 102 and a distal end 104. Proximal end 102 is coupled to a medical device 106, which may be an implantable medical device. Medical device 106 can be, for example, a stimulator configured to supply electrical stimulation therapy to target tissue, a drug pump that delivers drugs to a target site, or a sensor that senses parameters such as blood pressure, temperature, or electrical activity. The function of extending element 100 depends upon the function of medical device 106. When medical device 106 represents a drug pump and a reservoir for the drugs being delivered, for example, extending element 100 represents one or more catheters that administer the drugs to the cells, with distal end 104 being deployed proximate to the cells of concern.

For purpose of illustration, FIG. 7 depicts medical device 106 as a stimulator configured to deliver electrical stimulation to target tissue via electrodes 108. Extending element 100 is a lead that conducts stimulations generated by stimulator 106 to electrodes 108.

Lead 100 includes fixation mechanism 110. In FIG. 7, fixation mechanism 110 is similar to medical device 30 in FIG. 3, in that fixation mechanism 110 includes a plurality of tines or spurs 112 that protrude from a housing 114 and that operate as fixation structures. Tines or spurs 112 radially extend from housing 114 and include tines or spurs 112 that extend in different radial directions. For example, tine or spur 112A extends in a different radial direction than tine or spur 112B. In addition, fixation mechanism 110 includes tines or spurs 112 that are axially displaced from each other (e.g., tines or spurs 112A and 112B). Unlike medical device 30, however, fixation mechanism 110 is not a self-contained medical device. Fixation mechanism 110 holds electrodes 108 proximate to the target tissue to be stimulated.

Fixation mechanism 110 can be integrally formed with distal end of lead 104. For example, a portion of distal end 104, may be encased in silicone, and tines 112 and housing 114 can be made of the same materials. In another embodiment, fixation mechanism 110 can be embodied as a hollow sleeve sized to fit over a portion of distal end of lead 104.

Lead 100 can be deployed in a catheter according to conventional deployment procedures, with tines 112 in a collapsed configuration. When distal end 104 is proximate to the target tissue, the catheter can be withdrawn and tines 112 can expand to the extended configuration. In some implantations, lead 100 is disconnected from medical device 106 during deployment, and is coupled to medical device 106 after deployment.

Tines 112 of fixation mechanism 110 resist migration of distal end 104. In some deployments, the patient can naturally develop fibrous tissue around tines 112, which further promote anchoring of distal end 104 near the target tissue.

The preceding specific embodiments are illustrative of the practice of the invention. It is to be understood, therefore, that other expedients known to those skilled in the art or disclosed herein may be employed without departing from the invention or the scope of the appended claims. For example, the invention is not limited to an implant having the shape and illustrative dimensions described above.

Furthermore, the invention is not limited to the particular shapes of fixation structures elements depicted in the figures. Tines 14 in FIGS. 1 and 2, and tines 34 in FIG. 3 are depicted as having substantially rectangular cross-sections, but the invention supports fixation structures having other cross-sectional shapes. In addition, the invention encompasses embodiments in which the fixation structures extend further in one direction than in another.

Although the invention is described as useful in application with the neurostimulation, the invention is not limited to that application. Furthermore, the invention can be deployed via implantation techniques in addition to those described above. The invention further includes within its scope methods of making and using the implants described above.

In the appended claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:
1. An implantable medical device comprising:
a housing comprising a first end and a second end substantially opposite the first end;
an electrode coupled to the housing;
a pulse generator coupled to the electrode; and
a plurality of collapsible fixation structures coupled to the housing, wherein the collapsible fixation structures are configured to collapse in a first direction toward the first end of the housing and in a second direction toward the second end, wherein the fixation structures include flanges, and the flanges each comprise a plurality of ribs and webbing deployed between at least two of the ribs.
2. The device of claim 1, wherein the housing is constructed of at least one of silicone, polyurethane, titanium, stainless steel, fluoropolymer and hydrogel.

3. The device of claim 1, wherein at least one fixation structure is constructed of at least one of silicone, polyurethane, titanium, stainless steel, fluoropolymer and hydrogel.

4. The device of claim 1, wherein the housing is substantially cylindrical and has a diameter from one millimeter to seven millimeters.

5. The device of claim 1, wherein a length of the housing is from ten millimeters to twenty millimeters.

6. The device of claim 1, further comprising a power supply coupled to the pulse generator.

7. The device of claim 1, wherein the fixation structures include tines.

8. The device of claim 1, wherein the collapsible fixation structures are configured to assume a fully expanded state, wherein the housing defines an axis, and wherein the fixation structures are oriented substantially orthogonally from the axis when in the fully expanded state.

9. The device of claim 1, wherein the collapsible fixation structures are configured to assume a collapsed state, and wherein the device is sized to fit inside a bore of an insertion device.

10. The device of claim 9, wherein the insertion device comprises one of a needle, a hollow trocar, an endoscope, a catheter or a cannula.

11. The device of claim 1, wherein the collapsible fixation structures are configured to assume a fully expanded configuration, and wherein at least a portion of at least one fixation structure projects from one to seven millimeters from the housing when the fixation structure is in the fully expanded configuration.

12. The device of claim 1, wherein the device comprises an implantable neurostimulator.

13. The device of claim 1, wherein the device comprises an implantable physiological sensor.

14. The device of claim 1, wherein the electrode is deployed on a surface of at least one of the plurality of fixation structures.

15. The device of claim 1, wherein at least one of the plurality of collapsible fixation structures comprises a hydrogel fixation structure that expands in size upon contact with a fluid.

16. The device of claim 1, wherein at least one of the plurality of collapsible fixation structures is formed integrally with the housing.

17. The device of claim 1, wherein the housing defines an axis extending from the first end to the second end and the collapsible fixation structures are configured to assume a fully expanded state, and wherein, in the fully expanded state, at least one rib of the plurality of ribs extends further from the axis than the webbing extends from the axis.

18. An implantable medical device comprising:
a pulse generator means for generating an electrical stimulation;
a housing means for housing the pulse generator means, the housing means comprising a first end and a second end substantially opposite the first end;
an electrode means for delivering the electrical stimulation from the pulse generator means to a target tissue; and
a plurality of collapsible fixation means coupled to the housing means for restricting migration of the housing means when the housing means is implanted proximate to the target tissue, wherein the collapsible fixation means are configured to collapse in a first direction toward the first end of the housing means and in a second direction toward the second end, wherein the collapsible fixation means each comprise a flange, wherein the flange comprises a plurality of ribs and webbing deployed between at least two of the ribs.

19. The implantable medical device of claim 18, further comprising a power supply means coupled to the pulse generator means for supplying power to the pulse generator means.

20. The implantable medical device of claim 18, wherein the housing means defines an axis extending from the first end to the second end, wherein the collapsible fixation means are configured to assume a fully expanded state, and wherein, in the fully expanded state, at least one rib of the plurality of ribs extends further from, the axis than the webbing extends from the axis.

* * * * *

UNITED STATES PATENT AND TRADEMARK OFFICE
CERTIFICATE OF CORRECTION

Page 1 of 1

PATENT NO. : 8,489,189 B2
APPLICATION NO. : 10/977500
DATED : July 16, 2013
INVENTOR(S) : Carole A. Tronnes It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2496 days.

Signed and Sealed this
Thirteenth Day of January, 2015

Michelle K. Lee
*Deputy Director of the United States Patent and Trademark Office*